United States Patent [19]
Stevens

[11] Patent Number: 5,643,227
[45] Date of Patent: Jul. 1, 1997

[54] HEMOSTASIS CANNULA VALVE APPARATUS AND METHOD OF USING SAME

[76] Inventor: Robert C. Stevens, 18265 NW. Highway 335, Williston, Fla. 32696

[21] Appl. No.: 374,919

[22] Filed: Jan. 19, 1995

[51] Int. Cl.$^6$ .......................... A61M 5/00; A61M 25/00
[52] U.S. Cl. .................... 604/264; 604/167; 604/256; 604/247
[58] Field of Search ..................... 604/167, 256, 604/169, 237, 247, 264; 128/656, 658; 137/849; 251/149.1

[56] References Cited

U.S. PATENT DOCUMENTS

| | | |
|---|---|---|
| 4,000,739 | 1/1977 | Stevens . |
| 4,424,833 | 1/1984 | Spector et al. . |
| 4,430,081 | 2/1984 | Timmermans . |
| 4,610,665 | 9/1986 | Matsumoto et al. ............ 604/167 |
| 4,626,245 | 12/1986 | Weinstein . |
| 4,673,393 | 6/1987 | Suzuki et al. . |
| 4,895,565 | 1/1990 | Hillstead . |
| 4,929,235 | 5/1990 | Merry et al. .................. 604/167 |
| 5,000,745 | 3/1991 | Guest et al. .................. 604/256 |
| 5,009,391 | 4/1991 | Steigerwald . |
| 5,053,013 | 10/1991 | Ensminger et al. ............ 604/167 |
| 5,114,408 | 5/1992 | Fleischhaker et al. .......... 604/167 |
| 5,290,245 | 3/1994 | Dennis ........................ 604/167 |
| 5,304,156 | 4/1994 | Sylvanowicz et al. ........... 604/256 |

*Primary Examiner*—Robert A. Hafer
*Assistant Examiner*—V. Alexander
*Attorney, Agent, or Firm*—Fay, Sharpe, Beall, Fagan, Minnich & McKee

[57] ABSTRACT

A self-sealing valve arrangement for use in a hemostasis cannula includes a distal wiping gasket and an outer proximal tricuspid gasket bonded on a peripheral interface therebetween. The distal wiping gasket strips clots and fibrotic tissue from a catheter or vessel dilator as it is extracted from the hemostasis cannula preventing a disruptive accumulation of clots in the tricuspid valve.

2 Claims, 2 Drawing Sheets

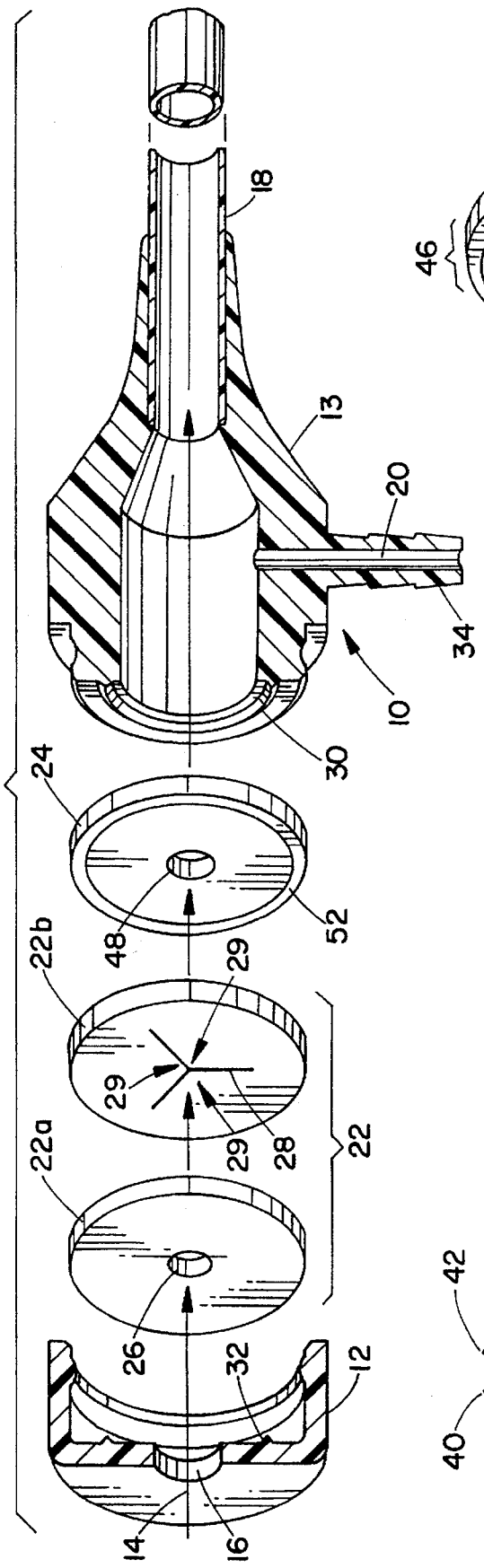
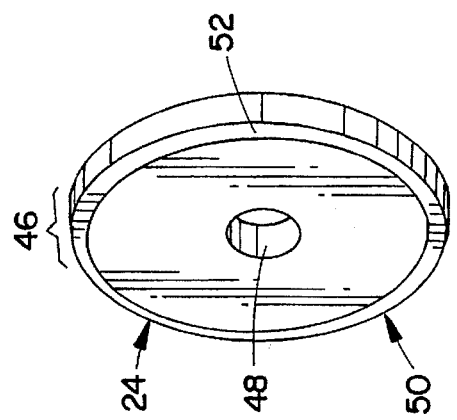
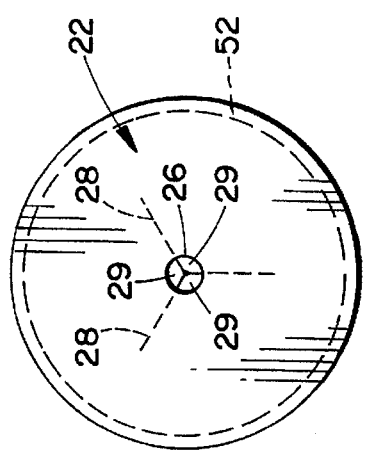
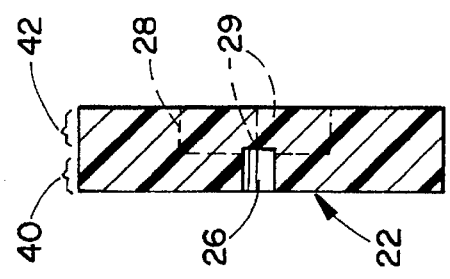

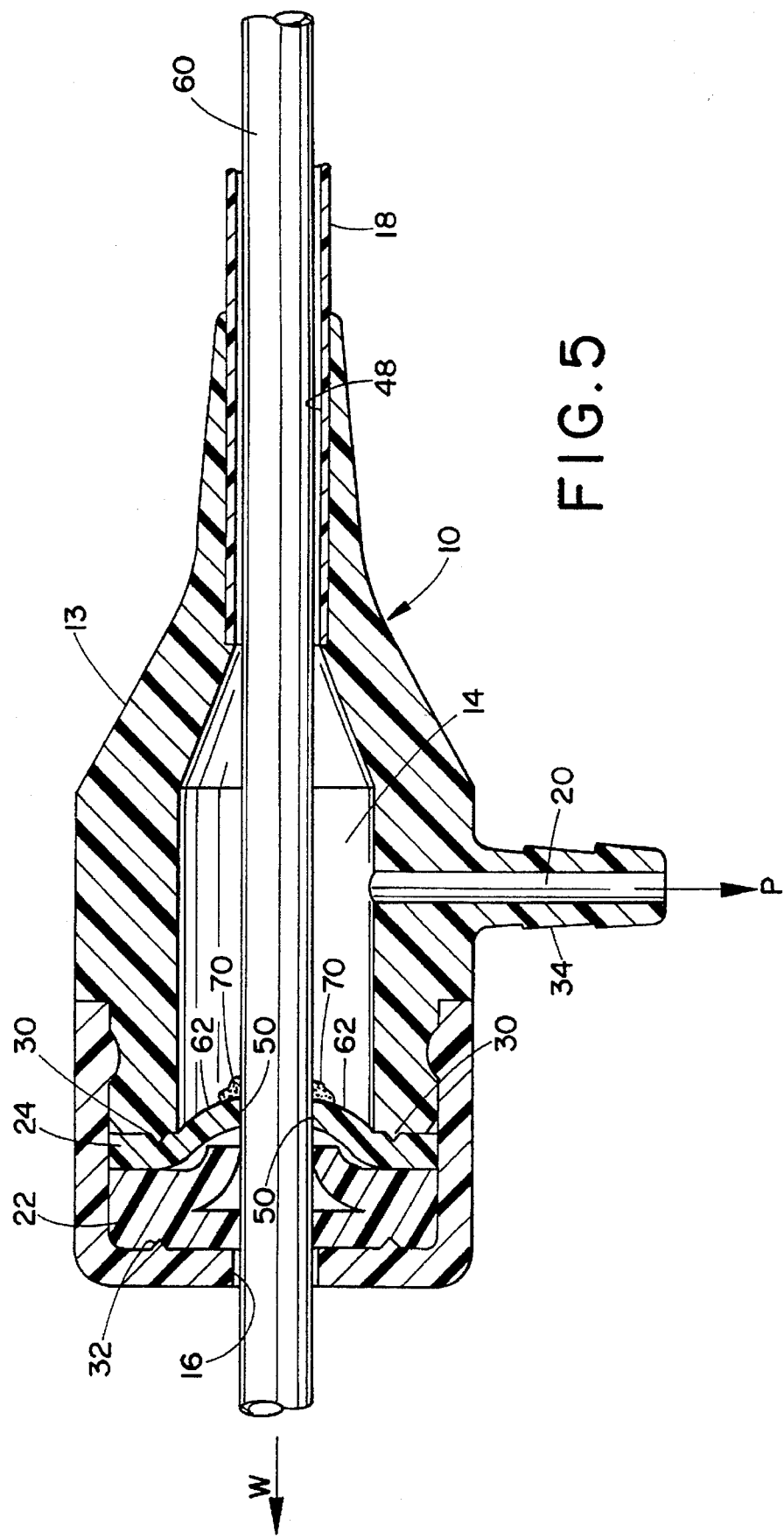

HEMOSTASIS CANNULA VALVE APPARATUS AND METHOD OF USING SAME

BACKGROUND OF THE INVENTION

This invention relates to improvements in valves for hemostasis catheter introducers used in the insertion and removal of catheters and guide wires from a patient's blood vessel. More particularly, the invention relates to a self-sealing gasket in a hemostasis cannula that prevents back bleeding with inserted catheter or guidewire devices and further prevents leakage from the cannula after removal of the catheter or guidewire devices.

Angiography is a well-known and very valuable procedure used to diagnosis vascular and organ disease. It involves the introduction of a hollow tubular catheter into one of the major arteries or veins, such as the femoral or brachial arteries, and advancing and maneuvering it into smaller branching vessels which are to be studied. After the catheter is in position, a radio-opaque fluid is injected through the catheter into the vascular system to be studied and an X-ray picture is taken of the now X-ray opaque vascular structure.

Prior art techniques for introducing such catheters include what is known as the "cut down" method and various modifications of the "Seldinger" technique. The "cut down" technique involves surgically opening a vein or artery and introducing the angiographic catheter directly through the incision. This method generally involves the loss of blood through the incision as well as venous ligation and arterial repair. The use of this method renders it particularly difficult to employ the same vessel when multiple studies are indicated.

*The American Journal of Cardiology*, VOLUME 30, Sep. 1972 at page 378, describes an alternative method of cardiac catheterization, a modification of the Seldinger technique, wherein a percutaneous sheath is introduced into the lumen of a blood vessel. A hollow needle is inserted through the skin and into the lumen; a guide wire is passed through the needle and advanced up the artery or vein into the organ to be studied; the needle is removed, leaving the guide wire in the vessel; a sheath and dilator unit are advanced over the wire into the vessel, and; the dilator is removed along with the guide wire. Thereafter, any type of catheter of similar diameter, can be inserted through the sheath into the vessel. To avoid excessive bleeding, and to ensure against the possibility of an air embolism, this technique requires the physician to occlude the orifice of the sheath during catheter changes. The procedure suffers from the possibility of a blood clot migrating to the heart, lungs, or extremities. Blood loss through the annular space between the sheath and the catheter is difficult to avoid.

My earlier invention, described in U.S. Pat. No. 4,000,739, provided a cannula which could be left in the vessel during angiographic or other catheterization procedures while the catheter is manipulated within the cannula and vessel. Generally, that invention featured a hemostasis cannula comprising a body having a passage therethrough adapted to receive a catheter and having a pair of juxtaposed gaskets mounted in the passage in contact with each other. A first one of the gaskets has a round hole, the other a Y-shaped slit. The first or more proximal gasket maintains a sealing relationship with the outer surface of the catheter and, upon withdrawal of the catheter from the passage, the gaskets cooperate to close the passage, since the distal gasket with the Y-shaped slit is compressed against the first gasket. The cannula described there further includes a length of flexible tubing in fluid tight engagement with the body. A port communicating with the body of the cannula for introducing fluids into the patients arteries is also provided.

Other valving arrangements have been demonstrated to be effective for use in catheter introducers such as that shown in U.S. Pat. No. 4,626,245 to Weinstein. There, the hemostasis valve comprises an elastomeric partition made of a single integral piece. A first slit is cut on a first side of the valve while a second slit is cut on the second, opposite side of the piece. The first and second slits are in intersecting relation to each other, each slit having a depth sufficient to permit physical interaction with each other but insufficient to extend through the entire thickness of the partition. The single piece construction of Weinstein sometimes resulted in leakage due to insufficient sealing around the catheter when inserted therethrough. Other leakage sometimes resulted from a build-up of clots between the slits preventing proper closure for a tight seal. This condition is aggravated when the catheter is left in the patient for extended periods.

U.S. Pat. No. 5,304,156 to Sylvanowicz, et al. describes a self-sealing gasket adapted to effect a seal when a catheter or guide wire extends through the gasket as well as when the gasket is empty. Sylvanowicz, et al. modified the gasket arrangement of Weinstein by providing a single piece molded gasket, the outer half thickness of the gasket having a central hole, slightly smaller in diameter than the diameter of the guide wire that will be received in the device for forming a seal about the guide wire. The inner half thickness of the gasket defines a plurality of radially extending slots which extend to a depth slightly greater than to the middle of the thickness of the gasket. The combination of slits and the central hole provide an arrangement which is effective to make a tight seal against a guide wire as well as with much larger diameter catheters without unduly inhibiting movement of either the guide wire or the catheter through the gasket.

Although the above gasketing arrangements are functional as far as preventing unnecessary blood loss while the catheter is inserted through the hemostasis cannula, modern medical practices have placed a new demand on cannula valves requiring additional performance levels which have heretofore been unaddressed. More particularly, the prior medical practice was to allow the hemostasis cannula to remain in place for several minutes or perhaps up to two hours. Currently, however, the cannula may be left in for many hours or over a period of several days at a time. Mainly, the current practice of leaving the hemostasis cannula in place for prolonged periods is for the purposes of facilitating follow-up procedures without the risk of re-entry into the vessel for access.

In practice, the valves used in hemostasis cannula leak to some extent. Even though most leaks are minor and usually not life threatening, they are irritating. Oftentimes, the tricuspid leaflets such as in the valve of my earlier patent identified above do not completely close because they do not perfectly mate. Small blood clots which form on the catheter lodge between the leaflets as the catheter is withdrawn from the cannula. When this happens, the tip of the catheter or vessel dilator must be re-introduced through the gasketing arrangement in order to realign the leaflets forming the tricuspid valve. In most instances, rearranging the leaflets prevents further leakage. However, when the cannula is left in place in a vein or artery of a patient for extended periods, fibrotic tissue can form clots that lodge between the leaflets of the tricuspid valve, causing leakage.

SUMMARY OF THE INVENTION

The present invention provides an improved valve for use in a hemostasis cannula system which overcomes the above-identified leakage problems presented by prior art valves. The self-sealing valve of the present invention includes a first, or proximal gasket molded in a single piece from a resilient material, preferably from a high durometer elastomer to have a predetermined thickness. The outer half thickness of the first gasket has a central hole, slightly smaller in diameter than the diameter of the catheter or vessel dilator that will be received in the device for forming a seal about the catheter or dilator. The inner half thickness of the proximal gasket includes a plurality of radially extending slots preferably of the tricuspid variety which extend to a depth of one half the thickness of the first gasket. The combination of the central hole and slits meet approximately at the mid-point of the first gasket to define an arrangement which is effective to form a seal around a catheter or vessel dilator without unduly inhibiting movement of the device through the gasket. The first gasket seals the cannula from leakage when the catheter or dilator is removed from the cannula by the closing action of the tricuspid valve leaflets.

The improved self-sealing valve of the present invention further includes an inner or proximal second gasket, preferably also molded from a high durometer elastomer, such as that forming the first gasket and including a central hole which, like the central hole formed in the first gasket is sized to be slightly smaller in diameter than the diameter of the catheter or vessel dilator expected to be received in the hemostasis cannula. The inner or proximal second gasket performs a wiping function to strip clots or fibrin from the catheter as it is withdrawn from the hemostasis cannula before they become lodged in the slits of the tricuspid valve. In addition, the second gasket effectively traps the tricuspid valve closed between two round hole gaskets to enhance the seal provided thereby when the catheter or vessel dilator is withdrawn from the hemostasis cannula.

The present invention is advantageous in that an improved self-sealing is provided through the interaction of a distal round hole wiping gasket adjacent a tricuspid proximal sealing gasket in the body of a hemostasis cannula. The distal gasket wipes clean the guide wire, catheter or vessel dilator as it is extracted from the hemostasis cannula body. After the catheter is extracted, the proximal tricuspid gasket seals the cannula body against leakage.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein:

FIG. 1 is an exploded, partially cut-away view of a hemostasis cannula using the self-sealing valve of the present invention;

FIG. 2 is an enlarged sectional illustration of the one-piece proximal first gasket element forming the self-sealing valve of the present invention;

FIG. 3 is an illustration of the first gasket as viewed from the left (proximal) face of FIG. 2;

FIG. 4 is an enlarged sectional illustration of the distal second gasket forming the self-sealing valve according to the present invention; and, FIG. 5 is a view in cross-section of the self-sealing valve embodiment of FIG. 1 with a catheter extending through the cannula.

DETAILED DESCRIPTION OF THE DRAWINGS

Referring now to the drawings wherein the showings are for the purposes of illustrating the preferred embodiment of the invention only and not for the purposes of limiting the same, the figures show a hemostasis cannula incorporating an improved self-sealing valve according to the present invention. As seen in FIG. 1, the cannula comprises a generally cylindrical hub or body portion 10 having a snap-on cap 12 and a tapered portion 13 leading to a length of flexible tubing 18 that functions as an introducer sheath. Within the body 10 is an axially extending center passage generally designated by arrow 14. The body portion 10 and the tube 18 may be made of any one of a number of well-known suitable plastic materials, e.g., high density polyethylene. A pair of gaskets 22, 24 are enclosed within the cap 12. Although preferably formed of a unitary construction, the proximal gasket 22 is illustrated in the FIG. 1 with its functional constituent parts 22a, 22b separated for ease of understanding. Overall, the proximal gasket 22 has a centrally positioned hole 26 in a first half portion 22a and a Y-slit 28 in a second half portion 22b centrally disposed therein. The first gasket 22 is preferably formed of silastic or other similar elastic material such as latex, silicon rubber, or other suitable bio-compatible sealing material. The hole 26 in the first gasket half has a diameter slightly less than that of a catheter or vessel dilator expected to be used with the cannula so that, when the catheter (not shown) is inserted through the passage 14, the gasket 22 will sealing engage it, as shown in FIG. 5. The first gasket also includes a Y-slit 28 in the second half portion 22b to permit relatively unobstructed passage of the catheter or vessel dilator therethrough. However, when the catheter or dilator is not in position within the cannula, the Y-slit 28 closes, resting up against the proximal half of the first gasket. In the closed position, the proximal gasket 22 withstands a minimum of 300 mm. blood pressure, thereby preventing any blood flow out of the cannula through the passage 14. The cap 12 has a centrally located hole 16, positioned co-axially with the gaskets 22, 24 and an annular ridge 32 which seals the gasket 22 against the cap 12. A second annular ridge 30 disposed on the body 10 likewise acts to seal the distal gasket 24.

Formed integrally with the body 10 is a boss 34 extending laterally outwardly from the body 10 and containing a passage 20 leading into the passage 14. The boss 34 is stepped on its exterior to provide means for connection to a plastic tube or the like for flushing the body 10 or introducing fluids or the like into the passage 14. A saline solution or other liquid may be introduced through the tube for flushing the interior of the cannula hub portion and cannula tubing, thus helping prevent clotting within the cannula or at the interface of the cannula and catheter in the patient's vessel.

As shown in enlarged detail in FIGS. 2 and 3, the proximal gasket 22 may be considered as having approximately an outer half thickness 40 in the first half region 22a and an inner half thickness 42 in the second half region 22b. The outer half thickness 40 is formed with the central aperture 26 that extends only to a depth of about half the overall thickness of the gasket 22. The inner half thickness 42 of the gasket is formed with a plurality of radially extending slits 28 that extend to a depth of about one half the thickness of the gasket 22. The slits 28 extend into the surrounding radial wall defining the central aperture 26 as shown in FIG. 2. The slits 28 define three approximately triangularly shaped flaps 29 that overlap the central aperture 26. The diameter of the central aperture 26 is selected so that it will effect a seal with the catheter or vessel dilator with which the device 10 will be used. The radially extending slits 28 on the distal face of the gasket 22 preferably extend radially a distance that is slightly greater than the maximum diameter of catheter with which the device is to be used.

In the preferred embodiment illustrated in FIGS. 2 and 3, the proximal gasket 22 is made by first molding a silastic disc (or other similar elastic material) to a thickness of approximately 0.50 inches. Next, the hole 26 is punched or otherwise formed in the outer face of the first gasket 22 to a depth of approximately 0.25 inches. The flaps 29 are formed on the inner side of the first gasket 22 by stamping three slits 28 to a depth of approximately 0.25 inches. The slits extend through the outer half thickness 42.

Next, with reference to FIG. 4, the second or distal gasket 24 may be considered as comprising an overall thickness 46 and formed with a central aperture 48 that extends completely through the thickness 46 of the gasket 24. In the preferred embodiment, the second gasket is formed by molding a silastic disc to a thickness of approximately 0.25 inches and then providing the central aperture 48 therein such as by a stamping process or the like.

With the first and second gaskets 22, 24 in hand, the second gasket 24 is molded around its perimeter 50 to the proximal gasket 22 at an interface 52 therebetween. It is important that the second gasket 24 be bonded to the first gasket 22 only around the perimeter in order to permit a full range of motion in the triangularly shaped flaps 29 on the first gasket. When the catheter or vessel dilator is inserted into the hemostasis cannula through the valve 10, the inner or distal gasket 24 separates slightly from the proximal gasket 22 permitting the flaps 29 to open therebetween in the direction of arrow 14. In the other direction, as the catheter is extracted from the cannula, the distal gasket 24 exerts a closing force on the flaps 29 of the first gasket 22 ensuring a tight seal. The flaps 29 are effectively "captured" between the gasket 24 and the snap-on cap 12.

The distal gasket 24 also performs a wiping action to scrape any fibrotic tissue or clots from the outer surface of the cannula, during removal/withdrawal thereof, as illustrated best in FIG. 5. Referring to that FIGURE, a catheter 60 is shown passing through the central hub or body portion 10 as well as through the first and second gaskets 22, 24. The triangularly shaped flaps 29 on the first gasket 22 are spread open or displaced by the physical body of the catheter 60. The distal gasket 24 snugly engages the outer surface of the catheter 60 at a continuous circumferential interface 50 as the catheter passes through the central aperture 48 thereof. As the catheter is withdrawn from the cannula in the direction marked W on FIG. 5, the inward facing surface 62 of the distal gasket 24 effects a scraping action on the outer surface of the catheter 60. Fibrotic tissue and clots 70 are thereby scraped from the catheter and prevented from entering into or between the slits 28 or flaps 29. When the catheter 60 is completely withdrawn from the cannula body 10, a small amount of blood may be purged through the body in a direction labeled P to effectively carry away the clots 70 from the body of the cannula.

The invention has been described with reference to the preferred embodiment. Obviously, modifications and alterations will occur to others upon a reading an understanding of this specification. It is my intention to include all such modifications and alterations insofar as they come within the scope of the appended claims or the equivalents thereof.

Having thus described the invention, I now claim:

1. A hemostasis cannula comprising:

a housing having an opening on an outer first end and an introducer sheath on an inner second end of the housing; and, a self-sealing gasket assembly mounted in the housing and including a unitary first member joined to a second member, the first member having a first surface facing said outer first end and a second surface facing said inner second end, at least three radially extending slits extending from the second surface part way into the first member, a first circular central aperture extending inwardly from said first surface and intersecting with said at least three radially extending slits, the second member having a circular second central aperture extending therethrough and substantially aligned with said first central aperture and located between said introducer sheath and said first member, and the second member joined directly to the periphery of the second surface of the first member, and wherein said first and second circular central apertures are of substantial equal diameter and related to the diameter of catheters or guidewire devices intended to be used therewith to provide a sealing and wiping action on such catheters or guidewire devices passing therethrough.

2. The hemostasis cannula according to claim 1 wherein:

the depth of said first central aperture is substantially equal to one-half the thickness of the first member; and the said slits extend into the first member a distance substantially equal to one-half the thickness of the first member.

* * * * *